US009265463B1

(12) United States Patent
Hipp et al.

(10) Patent No.: US 9,265,463 B1
(45) Date of Patent: Feb. 23, 2016

(54) METHODS FOR DETERMINING SPINE INSTABILITY AND FOR ELIMINATING THE IMPACT OF PATIENT EFFORT ON STABILITY DETERMINATIONS

(71) Applicant: Medical Metrics, Inc., Houston, TX (US)

(72) Inventors: John A. Hipp, Houston, TX (US); Nicholas Wharton, Houston, TX (US)

(73) Assignee: Medical Metrics, Inc., Houston, TX (US)

( * ) Notice: Subject to any disclaimer, the term of this patent is extended or adjusted under 35 U.S.C. 154(b) by 0 days.

(21) Appl. No.: 14/579,563

(22) Filed: Dec. 22, 2014

(51) Int. Cl.
*A61B 5/00* (2006.01)
*A61B 6/00* (2006.01)
*A61B 6/04* (2006.01)

(52) U.S. Cl.
CPC .............. *A61B 5/4566* (2013.01); *A61B 6/0492* (2013.01); *A61B 6/505* (2013.01)

(58) Field of Classification Search
CPC ................... A61B 6/032; A61B 6/505; G06T 2207/30012; G06T 2207/10116; G06T 2207/10081; G06T 7/0012; G06T 2207/10072; G06T 2207/30004; G06T 2207/30008
See application file for complete search history.

(56) References Cited

U.S. PATENT DOCUMENTS

| 8,724,865 B2 * | 5/2014 | Hipp ...................... G06T 7/0014 382/128 |
| 2009/0232378 A1 * | 9/2009 | Nakamura .............. G06T 7/003 382/131 |
| 2010/0310140 A1 * | 12/2010 | Schneider ............ G06K 9/6247 382/130 |
| 2011/0279650 A1 * | 11/2011 | Liao ....................... A01K 29/00 348/46 |

OTHER PUBLICATIONS

J. Dvorak et al., In Vivo Flexion/Extension of the Normal Cervical Spine, Journal of Orthopedic Research, Nov. 1991, p. 828-834, vol. 9, Issue 6, Raven Press, Ltd., New York.
Gary Ghiselli et al., Prospective Analysis of Imaging Prediction of Pseudarthrosis After Anterior Cervical Discectomy and Fusion, Spine, Mar. 15, 2011, p. 463-468, vol. 36, Issue 6, Lippincott Williams & Wilkins.
John A. Hipp et al., Defining Pseudoarthrosis in the Cervical Spine With Differing Motion Thresholds, Spine, Jan. 15, 2005, p. 209-210, vol. 30, Issue 2, Lippincott Williams & Wilkins.
Mehul Taylor et al., Observer agreement in assessing flexion-extension X-rays of the cervical spine, with and without the use of quantitative measurements of intervertebral motion, The Spine Journal, Jan. 15, 2007, p. 654-658, vol. 7, Issue 6, Elsevier Inc.
John A. Hipp & Nicholas D. Wharton, Quantitative Motion Analysis (QMA) of Motion-Preserving and Fusion Technologies for the Spine, Motion Preservation Surgery of the Spine: Advanced Techniques and Controversies: Expert Consult: Online and Print, 1e, Jun. 12, 2008, p. 85-97, Elsevier Inc.

(Continued)

*Primary Examiner* — Edward Park
(74) *Attorney, Agent, or Firm* — Chamberlain, Hrdlicka

(57) ABSTRACT

The present disclosure describes a method for determining spinal instability, more particularly, a method for quantifying the type and extent of spinal instability in a standardized way. The disclosure also describes a method comprising measurement of the intervertebral rotation and intervertebral translation between a vertebrae pair using simple images, and from these measurements, determining if one or more vertebrae pair of the spine is unstable. Finally, the disclosure describes software that may be used to quantify the type and extent of spinal instability.

45 Claims, 1 Drawing Sheet

(56) References Cited

OTHER PUBLICATIONS

Matthew S. Yeager et al., Reliability of computer-assisted lumbar intervertebral measurements using a novel vertebral motion analysis system, The Spine Journal, Feb. 1, 2014, p. 274-281, vol. 14, Issue 2, Elsevier Inc.

A.K. Dietz et al., Kinematics of the Aging Spine: A Review of Past Knowledge and a Survey of Recent Developments, with a Focus on Patient-Management Implications for the Clinical Practitioner, The Comprehensive Treatment of the Aging Spine, Dec. 2010, Chapter 10, p. 1-12, Elsevier Inc.

Gregory Schneider et al., Abnormal Motion in Spondylolytic Spondylolisthesis, Spine, May 15, 2005, p. 1159-1164, vol. 30, Issue 10, Lippincott Williams & Wilkins.

Dilip K. Sengupta et al., the Basis of Mechanical Instability in Degenerative Disk Disease, Spine, Jun. 1, 2014, p. 1032-1043, vol. 39, Issue 13, Lippincott Williams & Wilkins.

Taylor Brown et al., Intervertebral Motion After Incremental Damage to the Posterior Structures of the Cervical Spine, Spine, Sep. 1, 2005, p. E503-E508, vol. 30, Issue 17, Lippincott Williams & Wilkins.

P.J. Weiler et al., Analysis of Sagittal Plane Instability of the Lumbar Spine in Vivo, Spine, Dec. 1990, p. 1300-1306, vol. 15, Issue 12, Lippincott Williams & Wilkins.

Eythor Kristjansson et al., Increased Sagittal Plane Segmental Motion in the Lower Cervical Spine in Women With Chronic Whiplash-Associated Disorders, Grades I-II, Spine, Oct. 1, 2003, p. 2215-2221, vol. 28, Issue 19, Lippincott Williams & Wilkins.

Reginald J. Davis et al., Comparative Impact of Stabilization on Pre-Operative Hypermobility via Assessment of Clinical and 'Translation per Degree Rotation' Outcomes, Presented at Congress of Neurological Surgeons meeting, 2014.

M.T. Thompson et al., Brief report: validation of a system for automated measurement of knee laxity, Clinical Biomechanics, Mar. 2004, p. 308-312, vol. 19, Issue 3, Elsevier Inc.

L. Penning et al., Measurement of angular and linear segmental lumbar spine flexion-extension motion by means of image registration, European Spine Journal, Nov. 4, 2004, p. 163-170, vol. 14, Issue 2, European Spine Society.

Grigory Goldberg et al., Short-term Comparison of Cervical Fusion With Static and Dynamic Plating Using Computerized Motion Analysis, Spine, Jun. 1, 2007, p. E371-E375, vol. 32, Issue 13, Lippincott Williams & Wilkins.

Michael Derrick Selby et al., Radiologic Assessment of Spinal Fusion, Journal of the American Academy of Orthopaedic Surgeons, Nov. 2012, p. 694-703, vol. 20, Issue 11, American Academy of Orthopaedic Surgeons.

Daniel R. Fassett et al., Comparison of fusion assessment techniques: Computer assisted versus manual measurements, Journal of Neurosurgery. Spine., Jun. 2008, p. 544-547, vol. 8, Issue 6, American Association of Neurological Surgeons.

\* cited by examiner

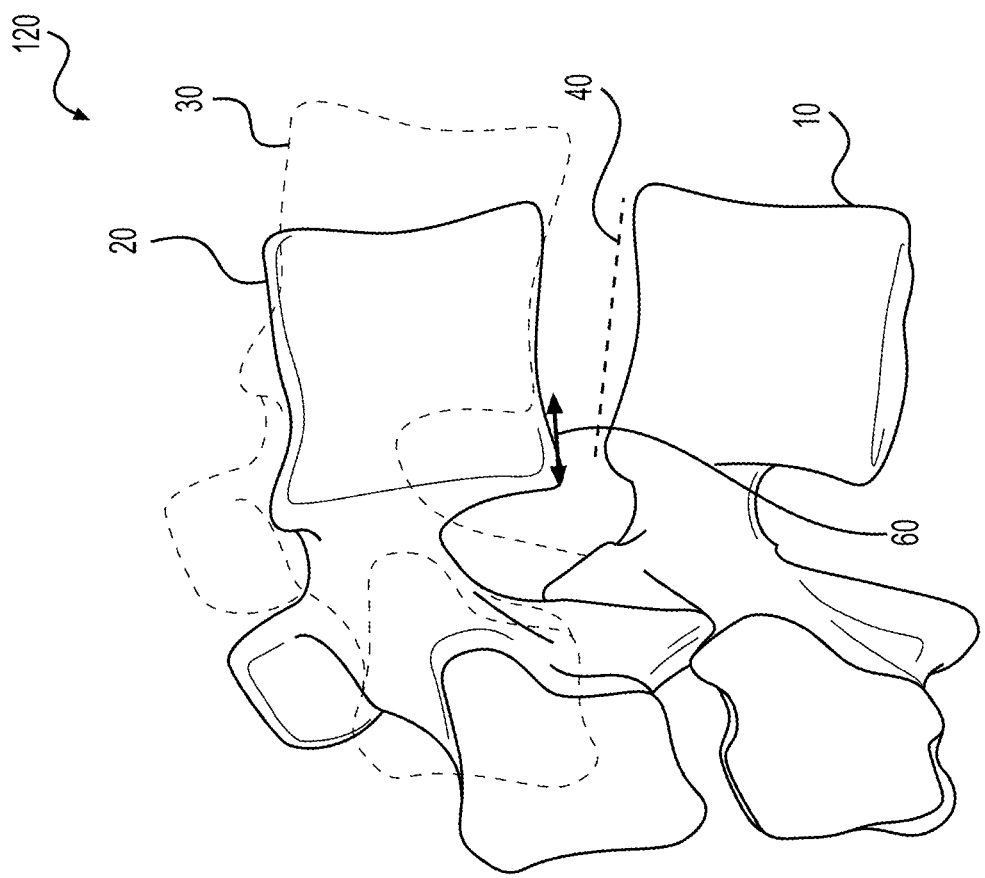
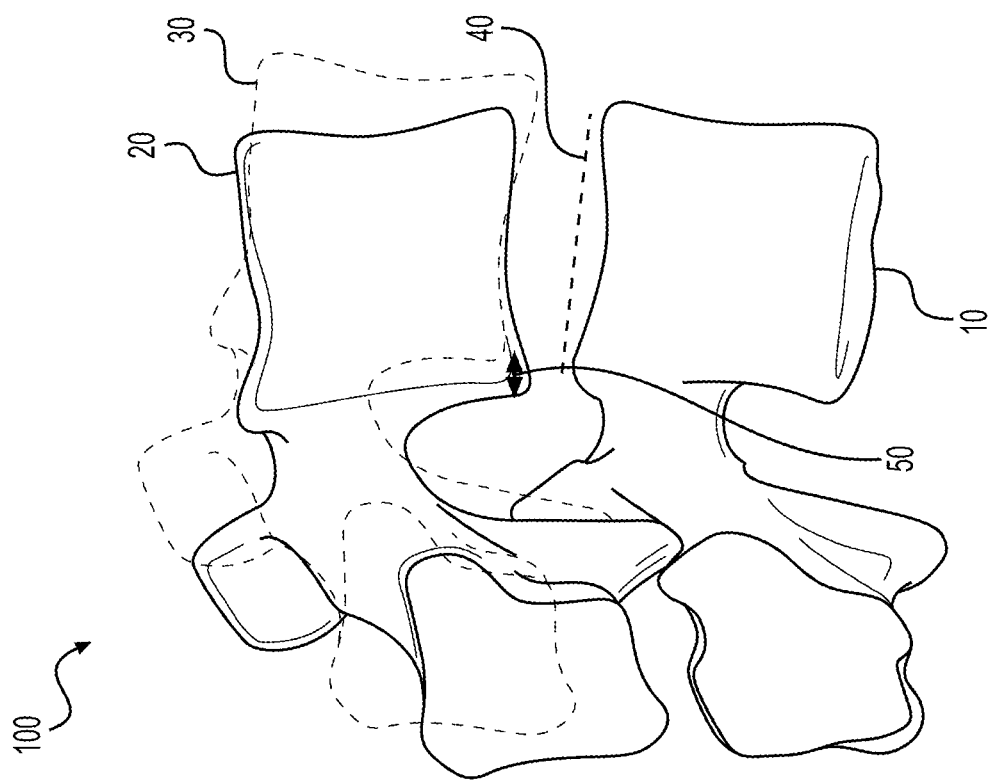

METHODS FOR DETERMINING SPINE INSTABILITY AND FOR ELIMINATING THE IMPACT OF PATIENT EFFORT ON STABILITY DETERMINATIONS

The present disclosure describes a method for determining spinal instability. More particularly, the disclosure describes a method for quantifying the type and extent of spinal instability in a standardized manner to inform a physician of the measure of instability as a number of standard deviations from an asymptomatic population. Still further, the disclosure describes a method comprising measurement of the intervertebral rotation and intervertebral translation between a vertebrae pair using simple images, and from these measurements, determining if one or more vertebrae pair of the spine is unstable.

Low back pain is one of the most common musculoskeletal complaints requiring medical attention. Millions of people annually seek medical solutions for low back pain. Because the causes of low back pain are so hard to diagnose and treat, many people are treated for long periods solely through pain management. Further, low back pain is one of the primary reasons given for disability or time away from a job. Given the significant economic impact that spinal disorders cause, it would be valuable to have a method for measuring and reporting spinal instability that is reliable, that is relatively inexpensive, that only requires information that is readily obtainable in a physician's office, that is easy to understand, and that can be measured in patients regardless of their effort, since people with back pain often make less effort than may be required to diagnose spinal instability using some methods.

Presently clinicians generally use physical tests and imaging studies to attempt to determine if motion in the spine is abnormal. The ability to correctly identify abnormalities in motion (the sensitivity), and the ability to correctly determine that there is no abnormality (the specificity) of the most common clinical tests are either not known, or have been shown by scientific studies to be unreliable or inaccurate in many patients. One of the most common methods used to assess motion in the spine is an imaging study using simple radiographs. In many cases, the clinician compares radiographs taken with the person in two or more different positions, to assess motion in the spine. Such a method can be highly unreliable and trained clinicians not infrequently disagree regarding how to interpret the assessed motion.

The other common method that has been used to measure motion between vertebrae in the spine involves combining geometric information obtained from a computed tomography (CT) study of the spine with information from a fluoroscopic imaging study of the spine. By knowing the actual three-dimensional geometry of an object, it is possible to estimate two-dimensional motion from fluoroscopic imaging data. Although this method is non-invasive, it does require a CT examination and substantial post-processing of the data. It is not a method that could be readily used in routine clinical practice.

Investigators have long attempted to define spinal instability. Despite the many research efforts, there is no standard, validated and objective measure of spinal instability. Intervertebral rotation and translation have been suggested as potential metrics for diagnosing spinal instability; however the significant variability between levels (e.g. L3-L4 vs L5-S1) and individuals has made it exceedingly difficult to classify measurements as normal or abnormal. Another problem with using rotation and translation as a metric comes from patient effort. To ascertain whether a patient's movement is asymptomatic, they would need to move as much (i.e., be as flexed or as extended) as the individuals did who were measured as part of the asymptomatic population. Otherwise, the measurements of translation and rotation will underestimate the true motion that can occur for each level.

Translation per degree of rotation (TPDR), has also been suggested as a metric for instability, specifically as a method to control for variability due to patient effort. It is recognized that damage or degeneration of the disc, facet joints and intervertebral ligaments can cause the amount of translation that occurs for a required rotation to increase. In the uninjured and non-degenerated spine there is an approximately linear relationship between translation and rotation, and the slope of this relationship is fairly similar between individuals.

Despite all of this work and a small number of studies reporting TPDR, no one has been able to develop a cohesive approach to diagnosing spinal instability. Further, no prior approach has come close to meeting any or all of the criteria for clinical diagnosis. For use in clinical diagnosis, the method must be accurate and reproducible, easy to understand, relatively inexpensive, and based upon information that is relatively easy to obtain regardless of the patient's condition. The method according to the present disclosure in its differing embodiments satisfies one or more of these criteria and, in at least one embodiment, satisfies all of these criteria.

According to a first embodiment, the present disclosure describes a method for calculating a spinal translation per degree of rotation (TPDR) that is independent of vertebrae size and does not require knowing the magnification of the image. This method of calculating TPDR allows direct comparison of a symptomatic population to an asymptomatic population. In one embodiment, the method includes, obtaining an x-ray film of a first and a second vertebrae in a first position; obtaining an x-ray film of a first and second vertebrae in a second position, wherein the degree of intervertebral rotation between the two positions is greater than 3 degrees; marking the position of at least one landmark on the first vertebra on the x-ray film of the first position; superimposing the two x-ray films and aligning the first vertebra and determining the rotation and translation required to align the second vertebra in the two x-ray films; measuring the degree of vertebral rotation between the first and second vertebrae in the first and second positions; measuring the translation of the landmark on the first vertebra between the first and second positions while holding the second vertebra fixed; normalizing the intervertebral translation measurement based upon a vertebral dimension; dividing the normalized intervertebral translation by the intervertebral rotation to give a TPDR.

In a second embodiment, the present disclosure describes a method of quantifying spinal instability by taking the TPDR and applying a standardizing formula specific to the vertebrae pair to generate a stability metric. According to this embodiment, an asymptomatic spine registers a value within a specific range and instability is displayed as a metric outside of the normal range. More specifically, the stability metric is reported as a number of standard deviations from "normal" where normal refers to a level appropriate value for an asymptomatic population.

In yet another embodiment, the present disclosure describes a non-transitory computer readable medium encoded with a computer program that, when executed by a processor, carries out a method for analyzing intervertebral motion of a spine, the method including, acquiring digital images of a first and a second vertebrae in a first position and a first and second vertebrae in a second position, wherein the degree of intervertebral rotation between the two positions is greater than 3 degrees; detecting or acquiring the position of at least one landmark on the first vertebra on the first image; electronically transferring the position of the at least one landmark on the first vertebra on the first image to the first vertebra on the second image; superimposing and aligning the two images on the first vertebra and determining the rotation and translation required to align the second vertebra in the two images; measuring the degree of vertebral rotation between the first and second vertebrae in the first and second positions; measuring the translation of the landmark on the first vertebra between the first and second positions while holding the second vertebra fixed; normalizing the intervertebral translation measurement based upon a vertebral dimension; dividing the intervertebral translation by the intervertebral rotation to give a translation per degree of rotation (TPDR) that is independent of vertebrae size; applying a standardizing formula to the TPDR specific to the first and second vertebrae (the vertebrae pair), to generate a stability metric reported as the number of standard deviations away from the same metric for an asymptomatic and radiographically normal population.

A better understanding of the various disclosed system and method embodiments can be obtained when the following detailed description is considered in conjunction with the drawings.

BRIEF DESCRIPTION OF THE DRAWINGS

FIG. 1 is a pair of vertebra on the left considered to be stable and a pair of vertebra on the right considered to be unstable.

The drawing FIGURES are not necessarily to scale. Certain features of the embodiments may be shown exaggerated in scale or in somewhat schematic form and some details of conventional elements may not be shown in the interest of clarity and conciseness.

DESCRIPTION

The following discussion is directed to various embodiments of the invention. Although one or more of these embodiments may be preferred, the embodiments disclosed should not be interpreted, or otherwise used, as limiting the scope of the disclosure, including the claims. It is to be fully recognized that the different teachings of the embodiments discussed below may be employed separately or in any suitable combination to produce desired results. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not structure or function.

In the following discussion and in the claims, the terms "including" and "comprising" are used in an open-ended fashion, and thus should be interpreted to mean "including, but not limited to."

As used herein, the terms "spinal stability" and "spinal instability" are understood to be interchangeable except where specifically indicated as different or where one of ordinary skill in the art would understand them to be different and refer to the deviations in the movement of the spine in a symptomatic patient when compared to an asymptomatic population.

As used herein, the terms "intervertebral translation" and "translation" are understood to be interchangeable except where specifically indicated as different or where one of ordinary skill in the art would understand them to be different and refer to the lateral or gliding movement of a vertebra. Translation rarely occurs by itself, but often accompanies other movements of the vertebrae.

As used herein, the terms "intervertebral rotation" and "rotation" are understood to be interchangeable except where specifically indicated as different or where one of ordinary skill in the art would understand them to be different and refer to the motion of a vertebra around an axis.

As used herein, the terms "standardized TPDR" and "stability metric" are understood to be interchangeable except where specifically indicated as different or where one of ordinary skill in the art would understand them to be different and refer to the TPDR that has been calculated using a normalized translation value and which has been multiplied by a standardizing formula.

The methods as described herein can be used to objectively quantify the quality of intervertebral motion and determine if the quality of motion is within normal limits defined by measurements in an asymptomatic and radiographically normal population. The methods as described herein reduce the impact of patient effort. More specifically, the methods as described herein overcome the limitations of prior art methods where the rotation derived from clinical flexion-extension studies may fail to detect abnormal rotation because the patient did not move enough to causes detectable abnormal rotation.

In healthy asymptomatic patients, i.e., in the absence of damage or degeneration, movement causes both intervertebral translation and intervertebral rotation to occur. Specifically, the wide range of human upper body motions that can occur in an asymptomatic person are made possible by controlled rotations between the vertebrae that comprise the spine. The magnitude of intervertebral translation that normally occurs between vertebrae is the minimum amount required to allow for the intended intervertebral rotation. Damage or degeneration of the normal mechanisms for controlling intervertebral rotation can result in abnormally high intervertebral translation for a given amount of rotation.

More specifically, the amount of intervertebral translation that occurs upon motion is a small fraction of, and linearly related to, the amount of intervertebral rotation. A sufficient magnitude of intervertebral rotation will yield a predictable intervertebral translation if the spine is healthy. When the degree of rotation between the adjacent vertebrae is greater than 3 degrees, the correlation as described herein provides an accurate predictor of spinal stability. According to one embodiment as described herein, the method requires a rotation between vertebrae in a pair that is at least 3 degrees although other threshold levels may be used, for example, at least 4 degrees, or at least 5 degrees.

FIG. 1 represents two digital images of each vertebral pair 100 and 120 in both the flexed and extended positions. As can be seen, the first vertebra 10 is superimposed over the same vertebra 10 in the associated digital image. The vertebrae 10 are held fixed while the second vertebra 20/30 is represented between the flexed and extended positions. In both vertebral pairs the solid lined vertebra 20 represents the vertebrae in the extended position. Likewise, the dotted line vertebra 30 represent the vertebrae in the flexed. When the rotation between the two images is kept fixed, the change in translation per degree of rotation can be visualized.

The dotted line over the endplate 40 defines the direction of the displacement of the vertebra as evidenced by the chosen landmark, e.g., the posterior inferior corner. As the image is moved in the direction of the line, the translation of the second vertebra 20/30 can be seen and is represented by the arrows 50 and 60. The arrow 50 shows a small translation which, in this instance, is consistent with stability of the spine for the represented vertebral pair. The long line 60 shows extended translation that in this instance is associated with instability for the represented vertebral pair.

While absolute rotation and translation provide individual metrics for the patient, they are very difficult to compare to an asymptomatic population to obtain relevant predictions of instability. Quantity of motion, i.e., absolute rotation and translation between vertebrae are frequently reported characteristics that can be helpful in comparing treatments in large populations of patients. However, the absolute quantity of motion is highly dependent on the patient effort when the flexion and extension images are obtained. In multiple clinical trials that have been analyzed, the clinical facility where flexion/extension x-rays were obtained explains as much or more of the variability in intervertebral rotation than any other single variable. The method as described herein minimizes the effect of patient effort by using the ratio of translation per degree of rotation (TPDR).

TPDR is calculated from the measurements of intervertebral translation and intervertebral rotation. TPDR can be calculated using any art recognized method for measuring intervertebral translation and intervertebral rotation. However, accurate and reproducible measurements facilitate the differentiation between normal and abnormal quality of motion. A preferred method for reliably and accurately measuring translation and rotation of the various vertebrae of the spine from images, e.g., x-ray films is described in U.S. Pat. No. 8,724,865 (hereinafter "the '865 patent"), which is incorporated herein by reference in its entirety. In the method described in the '865 patent, in a computer implemented form, radiographic films of a plurality of vertebrae are superimposed and aligned. The image alignment is carried out on the vertebra of interest using a pair of landmarks that are set in the first image and electronically transferred to the second image. The images are aligned based upon these landmarks. Once the images are aligned, one vertebra is held stationary. The images can then be toggled back and forth to see the movement of the second vertebra and the spine between the two positions, the positions generally being fully flexed and fully extended.

In the methods as described herein, the first and second position can be any two differing positions that are of interest. The method can be carried out on two images at different flex levels or images at different extension levels. Likewise the two positions can be something less than fully flexed and fully extended. For example, the images can be a comparison of 30 degrees of flex and 30 degrees of extension. It will be self-evident that additional data may be obtained from the comparison of more than two images for the same vertebral pair to improve the accuracy of the TPDR and other measurements.

In one embodiment as described herein, a method of characterizing spinal instability is disclosed using the imaging method as described in the '865 patent wherein the positions of landmarks are marked on the first film, the images are superimposed based upon adjusting the position of one image as the two images are alternately displayed until one vertebra remains in a constant position on the computer display, then repeating this process of adjusting the position of one image as the images are alternately displayed until a second vertebra is superimposed in the two images, then calculating a transformation matrix that describes the rotation and translation required to superimpose the second vertebra in the two images after first superimposing the first vertebra in the two images, and then using the transformation matrix to calculate the landmarks positions on the second film. By marking the films in this manner, the accuracy of the measurements can be maximized. In addition, difficulties in aligning the two films based upon the relative magnification and rotational position of the spine from one film to the other are addressed and minimized in the method described in the '865 patent.

The selection of at least one landmark is important only in so far as it allows consistent and reproducible measurement of translation and rotation in each patient and the asymptomatic population. Preferred landmarks for use in the disclosed methods may be chosen from the posterior superior corner of the vertebra, the centroid of the vertebra, or a specific anatomical feature found on the vertebra. The landmark that is used to measure the translation in patients must be the same landmark that is used to measure normal translation in the asymptomatic population. Accordingly a preferred landmark for measuring translation is the posterior superior corner of the vertebra. Use of this positional landmark has the added advantage that it provides a value that minimizes the effect of vertebra size. However, any chosen landmark may be corrected for vertebra size, so while posterior superior corner of the vertebra is a preferred embodiment, choice of another landmark is readily contemplated.

While the method of the '865 patent is a preferred method of measuring rotation and translation, the method as described herein may use fewer landmarks than described in the '865 patent. Variation from the '865 method are contemplated in the measurement methods as described herein and the method should only be as limited as it is defined in the instant claims.

From the two positions defined by the aligned images one can measure the intervertebral translation, the intervertebral rotation and the center of rotation. Center of rotation "COR" is well reported in the prior art and measurement methods are readily understood by the skilled artisan. As x-ray images are rarely taken at the same magnification or rotation, the center of rotation value is normalized to account for any differences in the size of the images. Any art recognized method can be used to normalize the center of rotation. According to one embodiment, the center of rotation can be normalized using the method described below with regard to the normalization of the translation value. Center of rotation can be abnormal in many ways, such as too posterior, too anterior, too cranial, too caudal or combinations of these. The COR coupled with the stability metric can provide a more complete picture to a physician regarding the nature of the instability or other abnormalities of the intervertebral motion.

In certain instances, the intervertebral motion can be paradoxical. Paradoxical motion is when for the level being measured moves in one direction, but the spine moves in the other. For example, the level being measured could move into a more flexed position while the spine moves into a more extended position. Corrections can be made for paradoxical motion using either an absolute value of the motion or a correction method as described below.

Correction can be done based on an x-ray of the spine in a neutral position. The correction that is applied is then dependent on whether only the neutral-to-flexion motion is paradoxical, whether only the neutral-to-extension motion is paradoxical, or whether both components of motion are paradoxical. In addition, the sign (positive or negative) of each component of motion is used to determine the correction. Table describes the algorithm.

| | Sign of Measure Rotation | | |
|---|---|---|---|
| Case | N to F | N to E | Total ROM Calculation |
| No paradoxical motion | − | + | N to E minus N to F |
| Both components paradoxical | + | − | N to F plus absolute value of N to E |
| One component paradoxical | + | + | Maximum of N to F or N to E |
| One component paradoxical | − | − | Maximum of absolute value of N to F or N to E |

Once the intervertebral translation is measured, it has to be normalized for the relative difference in size between the representations of the vertebra in the different images as described above with respect to center of rotation. X-ray images are rarely taken at the same magnification or rotation. Thus, the translation value will be affected by the differences in dimensions in the two radiographs. Accordingly, the translation value is normalized by looking at the difference in size between a feature of the vertebra shown in the first x-ray and the same feature of the same vertebra shown in the second x-ray. As the method is generally carried out as a computer implemented invention, a specific vertebral dimension is measured in the first x-ray and again in the second x-ray. The difference in pixel size is used to normalize the translation value. Any method for normalizing the size of the vertebral dimension can be used in the method as described herein The vertebral dimension may be any anatomical landmark that can be reliably measured in the two images. For example, the vertebral dimension may be chosen from one or more of endplate width, the height of the anterior or posterior edge of the vertebral body or a diagonal line across the vertebral body. According to one embodiment, normalization of the TPDR by the endplate width, for example, removes the influence of vertebral size on the TPDR and facilitates comparisons of data across different individuals.

With the measurement of rotation and normalized translation, the TPDR can be calculated by dividing the normalized intervertebral translation by the intervertebral rotation. Along with the TPDR, the center of rotation for each position can be measured and recorded. Other metrics that can be measured and presented include measured translation, measured rotation, specific coordinates of the center of rotation such as how far above or below the endplate or how far posterior or anterior to the middle of the vertebral endplate.

Each of the measured metrics can be standardized by multiplying the measured or calculated value by a standardizing value based upon the information taken from the asymptomatic population. For example, TPDR can be standardized to a stability metric or Z-score by subtracting from the measured TPDR the mean normal TPDR for the level being measured (e.g., L4-L5), and dividing that by the standard deviation for TPDR for the asymptomatic population for the level being analyzed. Standardizing TPDR by using level-specific normative TPDR data removes the level-dependency and allows the spinal stability to be represented simply as the number of standard deviations from normal. The mean and standard deviations used in calculating the standardized TPDR can be for a specific population such as young females to further refine the ability to differentiate normal from abnormal motion.

According to another embodiment of the methods as described herein, the landmarks may be chosen to improve sensitivity and selectivity of the TPDR calculation. More particularly, one may select certain landmarks and translation directions that would be the best indicators of the anticipated condition. For example, an avulsion injury of the outer annulus might be best detected by measuring the displacement as the change in disc height between flexion and extension and dividing that by rotation. Landmarks could be placed on specific anatomic landmarks of the spinous processes and displacements between the spinous processes could be expressed as displacement per degree of rotation to help detect injuries to the interspinous process ligaments.

Although the present disclosure frequently references obtaining and analyzing x-rays for generating the digital images, a person skilled in this field will appreciate that the images could be obtained with magnetic resonance imaging, computed tomography or other methods and analyzed using the methods described.

The method as described herein can be used in clinical diagnosis of symptomatic patients, in clinical trials of devices, technologies to treat spinal disorders, and in the continued care of individuals with spinal devices.

The method of the instant disclosure can be used in clinical studies to establish the baseline stability of one or more motion segments in the spine to determine if a patient satisfies specific inclusion and exclusion criteria relating to the initial stability of a motion segment. Further, the methods can be used to determine if an intervention can effectively provide stability to an initially unstable motion segment, to determine if an intervention may adversely affect the stability of a motion segment, either at the treatment or adjacent levels, and to determine if the initial stability of a motion segment can help to determine the future clinical success or failure of a treatment. In clinical settings the methods as described may be used to diagnose specific sources of back pain and to determine the best treatment options for each patient.

EXAMPLE

Generation of Asymptomatic Population Data 161 asymptomatic volunteers were measured at 647 radiographically normal levels and TPDR was obtained. The measurements were made using 510K approved software, QMA®, a Medical Metrics product. The results are set forth in Table 1.

TABLE 1

| Level | Mean | UL |
|---|---|---|
| L1-L2 | 0.51 | 0.76 |
| L2-L3 | 0.56 | 0.78 |
| L3-L4 | 0.60 | 0.81 |
| L4-L5 | 0.54 | 0.47 |
| L5-S1 | 0.18 | 0.47 |

Table 1 provides the ratio of intervertebral translation (normalized to endplate width) per degree of translation (TPDR). The left-most column provides the 95% confidence interval. These data include only radiographically normal levels. The TPDR data in Table 1 cannot be used as reference data for comparison using any alternative measurement method. As will be understood by the skilled artisan, if the measurement method for translation and rotation is changed, the asymptomatic population must be re-measured using the changed method.

Stability Metric Reliability

The method as described herein is well supported and has been compared with other known indicators of instability and has proven predictive.

Standardized TPDR results, stability metrics, were calculated for different patient populations where radiographic data was available. The following correlations were found between the standardized TPDR results and other indicators of instability.

Standardized TPDR was elevated in the presence of the facet fluid sign. Facet fluid sign is considered to be one of the best currently available indicators for instability. In addition, standardized TPDR was found to be abnormally high preoperatively in a substantial proportion of lumbar fusion patients. Instability would be expected in some of those patients since instability is considered a primary indication for spine fusions. Standardized TPDR measured before treatment has also been found to be predictive of patient outcome following treatment and these types of findings can help to determine the best treatment for a patient.

Standardized TPDR as described herein can be analyzed and reported as a binary (stable vs unstable) variable, or it can be analyzed as a continuous variable. This allows for a wider range of statistical tests to be used for data analysis. In addition, change in standardized TPDR over time or from a baseline can be used to detect of trends toward or away from instability. This can be used to determine if the spine is becoming unstable following decompression surgery or if a level adjacent to a fusion is becoming unstable after the fusion surgery.

Other embodiments of the present invention can include alternative variations. These and other variations and modifications will become apparent to those skilled in the art once the above disclosure is fully appreciated. It is intended that the following claims be interpreted to embrace all such variations and modifications.

What is claimed is:

1. A method for calculating a spinal translation per degree of rotation (TPDR) comprising:
    obtaining an x-ray film of a first and a second vertebrae in a first position;
    obtaining an x-ray film of a first and second vertebrae in a second position,
    wherein the degree of intervertebral rotation between the two positions is greater than 3 degrees;
    marking the position of at least one landmark on the first vertebra on the x-ray film of the first position;
    superimposing the two x-ray films and aligning the first vertebra and then determining the rotation and translation required to subsequently align the second vertebra;
    measuring the degree of vertebral rotation between the first and second vertebrae in the first and second positions;
    measuring the translation of the landmark on the first vertebra between the first and second positions while holding the second vertebra fixed;
    normalizing the intervertebral translation measurement based upon a vertebral dimension;
    dividing the normalized intervertebral translation by the intervertebral rotation to give a TPDR.

2. The method of claim 1, wherein the at least one landmark is chosen from the posterior superior corner of the vertebra, the centroid of the vertebra, or a specific anatomical feature found on the vertebra.

3. The method of claim 2, wherein the vertebral dimension used is the endplate.

4. The method of claim 2, wherein the posterior inferior corner is marked on the first film and is replicated electronically on the second film.

5. The method of claim 1, wherein the vertebral dimension used is the endplate.

6. The method of claim 1, wherein superimposing the two x-ray films to align the second vertebra further comprises electronically transferring the selected landmark to the second x-ray film.

7. The method of claim 1, further comprising selected at least one second landmark on the first x-ray film and electronically transferring the selected landmark to the second x-ray film; wherein the second landmark is used to establish the direction of translation.

8. The method of claim 1, wherein the method is a computer implemented method and the x-ray films are digital.

9. The method of claim 1, wherein the first position is a flexed position and the second position is an extended position.

10. The method of claim 1, wherein the first position is an extended position and the second position is a flexed position.

11. The method of claim 1, wherein the first and second position are both flexed or both extended.

12. The method of claim 1, further comprising,
    determining if the TPDR is within normal limits when compared to a standard that is defined by measurements in asymptomatic and radiographically normal individuals for the same first and second vertebra along the spine.

13. The method of claim 1, wherein the at least one landmark on the first film is replicated electronically on the second film using one or more of recognition or image stabilization.

14. A method for quantifying spinal stability comprising:
    obtaining an x-ray film of a first and a second vertebrae in a first position;
    obtaining an x-ray film of a first and second vertebrae in a second position, wherein the degree of intervertebral rotation between the two positions is greater than 3 degrees;
    marking the position of at least one landmark on the first vertebra on the x-ray film of the first position;
    superimposing the two x-ray films and aligning the first vertebra and determining the rotation and translation required to align the second vertebra;
    measuring the degree of vertebral rotation between the first and second vertebrae in the first and second positions;
    measuring the translation of the landmark on the first vertebra between the first and second positions while holding the second vertebra fixed;
    normalizing the intervertebral translation measurement to a vertebral dimension;
    dividing the normalized intervertebral translation by the intervertebral rotation to give a TPDR; and
    multiplying the TPDR by a standardizing factor specific to the first and second vertebrae to generate a stability metric wherein an asymptomatic spine is at zero and instability is displayed as a positive or negative value.

15. The method of claim 14, wherein the at least one landmark is chosen from the posterior superior corner of the vertebra, the centroid of the vertebra, or a specific anatomical feature found on the vertebra.

16. The method of claim 15, wherein the vertebral dimension used is the endplate.

17. The method of claim 14 wherein the vertebral dimension used is the endplate.

18. The method of claim 14, wherein superimposing the two x-ray films to align the second vertebra further comprises electronically transferring the selected landmark to the second x-ray film.

19. The method of claim 14, further comprising selected at least one second landmark on the first x-ray film and electronically transferring the selected landmark to the second x-ray film, wherein the second landmark is used to establish the direction of translation.

20. The method of claim 19, further comprising marking the position of the posterior inferior corner of the second vertebra on the second film; and measuring the intervertebral rotation between the first and second marks.

21. The method of claim 19, wherein the posterior inferior corner is marked on the first film and is replicated electronically on the second film.

22. The method of claim 14, wherein the method is a computer implemented method and the x-ray films are digital.

23. The method of claim 14, wherein the x-ray films are obtained from individuals with limited motion.

24. The method of claim 14, wherein the first position is a flexed position and the second position is an extended position.

25. The method of claim 14, wherein the first position is an extended position and the second position is a flexed position.

26. The method of claim 14, wherein the first and second position are both flexed or both extended.

27. The method of claim 14, further comprising,
determining if the TPDR is within normal limits when compared to a standard that is defined by measurements in asymptomatic and radiographically normal individuals for the same first and second vertebra along the spine.

28. The method of claim 14, wherein the at least one landmark on the first film is replicated electronically on the second film using one or more of recognition or image stabilization.

29. The method of claim 14, wherein the measured TPDR is reported along with one or more of intervertebral translation, intervertebral rotation, center-of-rotation or another metric to provide for a comprehensive assessment of the quantity and quality of intervertebral motion.

30. The method of claim 29, wherein one or more of the reported metrics is multiplied by a standardizing factor specific to the metric such that each standardized metric can be interpreted as a number of standard deviations away from the same metric for an asymptomatic and radiographically normal population.

31. A non-transitory computer readable medium encoded with a computer program that, when executed by a processor, is configured to control a method for analyzing intervertebral motion of a spine, the method comprising:
acquiring digital images of a first and a second vertebrae in a first position and in a second position, wherein the degree of intervertebral rotation between the two positions is greater than 3 degrees;
detecting or acquiring the position of at least one landmark on the first vertebra on the first image;
electronically transferring the position of the at least one landmark on the first vertebra on the first image to the first vertebra on the second image;
superimposing and aligning the two images on the first vertebra and determining the rotation and translation required to align the second vertebra in the two images;
measuring the degree of vertebral rotation between the first and second vertebrae in the first and second positions;
measuring the translation of the landmark on the first vertebra between the first and second positions while holding the second vertebra fixed;
normalizing the intervertebral translation measurement based upon a vertebral dimension;
dividing the intervertebral translation by the intervertebral rotation to give a normalized translation per degree of rotation (TPDR) that is independent of vertebrae size;
multiplying the TPDR by a standardizing factor specific to the first and second vertebrae (the vertebrae pair), to generate a stability metric reported as a number of standard deviations away from the same metric for an asymptomatic and radiographically normal population.

32. The computer readable medium of claim 31, further comprising,
detecting or acquiring at least one second landmark, wherein the second landmark is used to establish the direction of translation.

33. The computer readable medium of claim 31, further comprising acquiring or detection TPDR data on an asymptomatic population.

34. The computer readable medium of claim 33, wherein the standardizing factor for TPDR is calculated from the measured TPDR and the mean TPDR for the same vertebrae pair for an asymptomatic population.

35. The computer readable medium of claim 33, wherein the standardizing factor for TPDR is the measured TPDR minus the mean TPDR of the same vertebrae pair for an asymptomatic population divided by the standard deviation for the TPDR at the same vertebrae pair for an asymptomatic population.

36. The computer readable medium of claim 35, wherein the vertebral dimension used is the endplate.

37. The method of claim 35, wherein the first position is a flexed position and the second position is an extended position.

38. The method of claim 35, wherein the first position is an extended position and the second position is a flexed position.

39. The method of claim 35, wherein the first and second position are both flexed or both extended.

40. The computer readable medium of claim 35, further comprising,
determining if the TPDR is within normal limits when compared to a standard that is defined by measurements in asymptomatic and radiographically normal individuals for the same first and second vertebra along the spine.

41. The computer readable medium of claim 35, wherein the at least one landmark on the first film is replicated electronically on the second film using one or more of recognition or image stabilization.

42. The computer readable medium of claim 35, further comprising,
reporting TPDR along with one or more of intervertebral translation, intervertebral rotation, center-of-rotation or another metric to provide for a comprehensive assessment of the quantity and quality of intervertebral motion.

43. The method of claim 42, wherein one or more of the reported metric is multiplied by a standardizing factor specific to the metric such that each standardized metric can be interpreted as a number of standard deviations away from the same metric for an asymptomatic and radiographically normal population.

44. The computer readable medium of claim 31, wherein the at least one landmark is chosen from the posterior superior corner of the vertebra, the centroid of the vertebra, or a specific anatomical feature found on the vertebra.

45. The computer readable medium of claim 44, wherein the vertebral dimension used is the endplate.

\* \* \* \* \*